United States Patent [19]

Alvarez et al.

[11] 4,029,963

[45] June 14, 1977

[54] X-RAY SPECTRAL DECOMPOSITION IMAGING SYSTEM

[75] Inventors: Robert E. Alvarez, Stanford; Albert Macovski, Palo Alto, both of Calif.

[73] Assignee: The Board of Trustees of Leland Stanford Junior University, Stanford, Calif.

[22] Filed: July 30, 1976

[21] Appl. No.: 710,359

[52] U.S. Cl. .............................. 250/360; 250/369; 250/445 T; 250/510

[51] Int. Cl.² ................. A61B 6/02; G01N 23/08; H05G 1/30

[58] Field of Search .............. 250/360, 369, 445 T, 250/510

[56] References Cited

UNITED STATES PATENTS 3,965,358  6/1976  Macovski .......................... 250/369

*Primary Examiner*—Paul L. Gensler
*Assistant Examiner*—T. N. Grigsby

[57] ABSTRACT

Projection measurements are made of the transmitted x-ray beam in low and high energy regions. These are combined in a non-linear processor to produce atomic-number-dependent and density-dependent projection information. This information is used to provide cross-sectional images which are free of spectral-shift artifacts and completely define the specific material properties.

22 Claims, 8 Drawing Figures

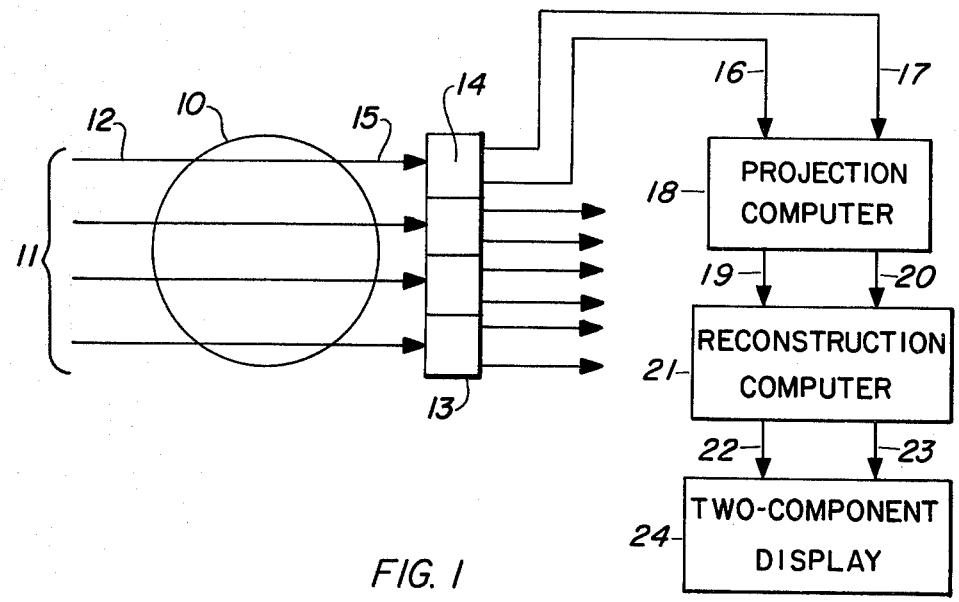
FIG. 1
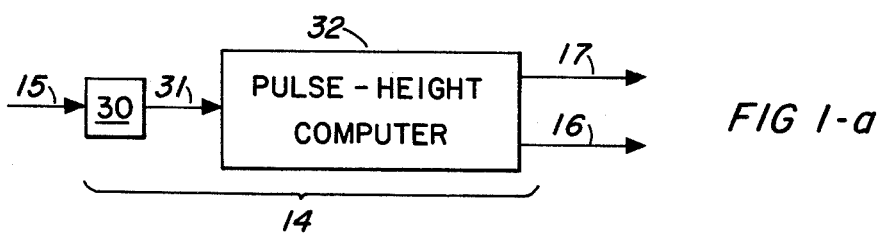
FIG 1-a
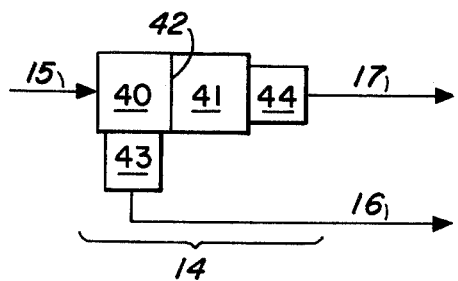
FIG. 1-b
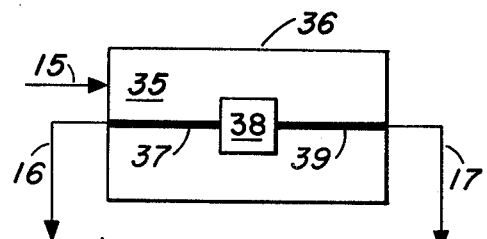
FIG. 1-c
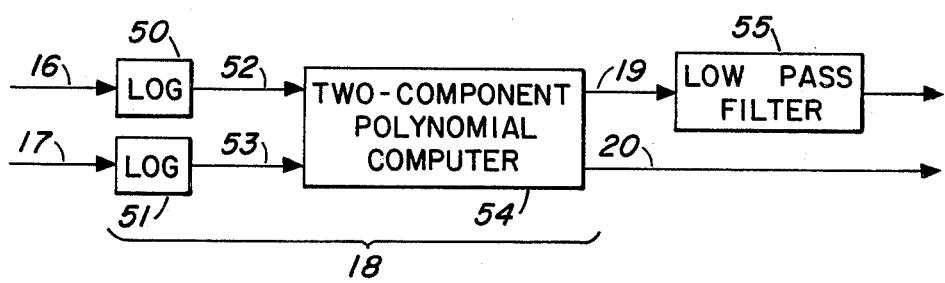
FIG. 1-d

X-RAY SPECTRAL DECOMPOSITION IMAGING SYSTEM

The invention described herein was made in the course of work under a grant from the Department of Health, Education, and Welfare.

BACKGROUND OF THE INVENTION

1. Field of the Invention

This invention relates to x-ray imaging systems. In a primary application the invention relates to obtaining cross-sectional x-ray images which are free of spectral-shift artifacts and providing information about the materials in the cross section. In another application the invention relates to defining the materials in a projection radiograph.

2. Description of Prior Art

A number of computerized tomography instruments have recently been introduced which produce x-ray cross-sectional images of the human anatomy. This is accomplished by measuring the x-ray projections at a number of different angles and using various mathematical techniques to reconstruct the three-dimensional information. The system of the EMI brain scanner is described in papers by J. Ambrose and G. N. Hounsfield in the *British Journal of Radiology*, vol. 46, 1973, on pp. 1023–47 and 1016–1022.

One of the biggest sources of inaccuracy of these instruments is the spectral shift of the x-ray beam energy as it tranverses the various materials in the cross-sectional slice. The log of the measured transmitted intensity should represent the sum or line integral of the linear attenuation coefficients along the x-ray beam. This will be the case if a monoenergetic source is used. These sources, however, have insufficient strength to provide a complete scan in a reasonable time interval. The use of broadband of polychromatic x-ray sources, which have sufficient strength, results in various non-linear artifacts since the attenuation coefficients are a function of energy. As the x-ray beam goes through different amounts and types of material, it has a different emerging energy spectrum which results in different measured attenuation coefficients. This is described in, "An Evaluation of the Quantitative and Radiation Features of a Scanning X-Ray Transverse Axial Tomograph," by E. C. McCullough, et al., in *Radiology*, vol. 111, June 1974, on pages 709–715.

In an attempt to minimize this problem most instruments have done one or both of two remedies; the use of path-length compensators, and the use of relatively high x-ray energies. Unfortunately, these remedies are only partial cures to the artifact problem. In addition, the use of pathlength compensators increases the radiation to the patient. The use of relatively high x-ray energies results in the loss of important information about the photo-electric component of the attenuation coefficient which helps to distinguish various types of tissue.

When a path-length compensator is used, with its associated increased radiation dose, the spectral-shift artifact can be corrected if the object being studied consists solely of two materials, such as a specific type of bone and soft tissue. Some instruments use corrections of this type. This correction breaks down, however, due to the wide variations in the types of bone and soft tissue.

A system for providing a general correction of this problem is described in U.S. Pat. No 3,965,358 issued to A. Macovski entitled, "Cross-Sectional Imaging System Using a Polychromatic X-Ray Source." In this patent a number of spectral measurements are taken of the transmitted x-ray beam. These are processed to produce a cross-sectional image which is free of spectral-shift artifacts. In addition, rather than producing a single-component image as is done in existing instruments, a number of images are obtained indicative of the specific materials in the cross-section.

This patent failed to recognize, however, that, to a high degree of accuracy, the linear attenuation coefficient of most materials found in the body can be decomposed into a photoelectric component which is strongly dependent on the atomic number and a Compton-scattering component which is primarily dependent on density. These components can be reconstructed from relatively simple low-energy and high-energy transmission measurements using non-linear processing. Thus the spectral-shift artifact is removed and each material in the cross section is defined in terms of its average atomic number and its density. This system is described in a paper authored by the inventors, R. E. Alvarez amd A. Macovski, entitled, "Utilization of Simple Energy Spectrum Measurements In X-Ray Computerized Tomography," published in the Proceedings of the Conference on Image Processing for 2D and 3D Reconstruction from Projections, Aug. 4, 1976.

The same general technique can be used conventional projection radiography for providing additional information about the materials in the object being studied. In projection radiography we are limited to finding the line integrals of the attenuation coefficients at each point. These represent the product of the attenuation coefficient and the path length over the entire path. If the projection is taken at different energies, using appropriate processing, separate images can be generated representing the line integral, or path lengths, of different materials in the object being studied. A system of this type is described in U.S. Patent 3,848,130 by A. Macovski entitled, "Selective Material X-Ray Imaging System." As in the case with computerized tomography, this patent failed to recognize that the linear attenuation coefficient can be decomposed into a photoelectric component and a Compton-scattering component based on two spectral measurements. This provides a simpler, two-component decomposition of the projection information.

SUMMARY OF THE INVENTION

An object of the invention is to provide apparatus for obtaining accurate cross-sectional images of an object using a polychromatic x-ray source. A further object of this invention is to eliminate the use of path length compensators which increase the radiation dose. A further object of this invention is to provide a simple means of making a spectral analysis of the x-ray transmission. A further object of this invention is to provide images representing the atomic number and density of the materials in the object being studied.

Briefly, in accordance with the invention, projection measurements are made of the x-ray transmission at low and high energies. Using non-linear processing, the line integrals of the atomic-number-dependent and density-dependent information is computed. In computerized tomography systems these are used to reconstruct two cross-sectional images which are free of artifacts and define the various materials. In projection radiography the line-integrals themselves are used to form two images which define the path lengths of the materials in the object.

BRIEF DESCRIPTION OF THE DRAWINGS

For a more complete disclosure of the invention, reference may be made to the following detailed description of several illustrative embodiments thereof which is given in conjunction with the accompanying drawings, of which:

FIG. 1 is a block diagram of an embodiment of the invention using an energy-selective detector;

FIG. 1-a is a schematic representation of one example of an energy-selective detector using pulse-height analysis;

FIG. 1-b is a schematic representation of another example of an energy-selective detector using integration;

FIG. 1-c is a schematic representation of another example of an integrating energy-selective detector using a gaseous chamber;

FIG. 1-d is a schematic representation of a projection computer;

DESCRIPTION OF THE PREFERRED EMBODIMENT

Figure 2:
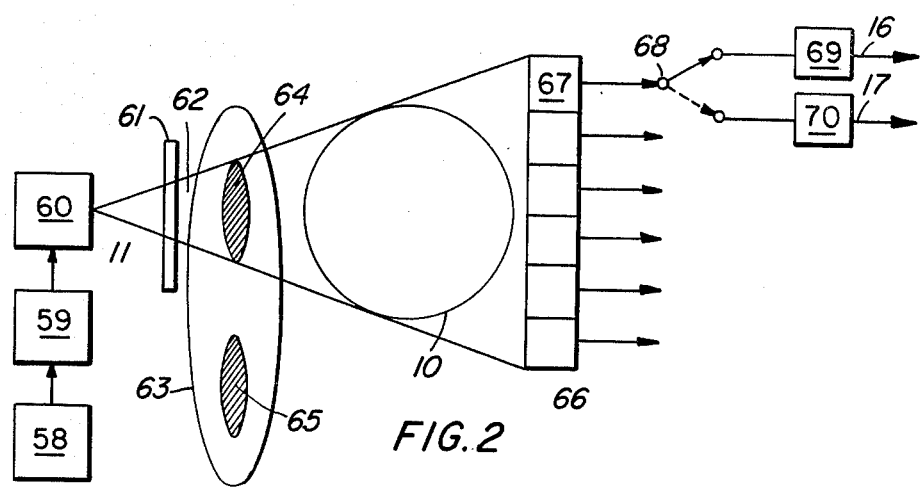
FIG. 2 is a schematic representation of an embodiment using sequential filtering.

An understanding of the broad aspects of the invention may best be had by reference to FIG. 1 of the drawings. A cross-sectional image is being made of object 10 which, for example, can represent some region of the human anatomy. A sheet beam of polychromatic x-rays 11, derived from a collimated source, is transmitted through the cross section of interest and detected by energy-selective detector array 13. Alternatively a single beam 12 can scan the cross section and be detected by the scanning energy-selective detector 14. For the purposes of this invention, these systems are equivalent. The system will be described considering only energy-selective detector 14 with the understanding that it represents either a scanned energy-selective detector, or one of the detectors of array 13, where the other detectors are used in an identical fashion.

It is desired to decompose transmitted beam 15 into detected low-energy and high-energy components so as to measure the object transmission in these two spectral regions. A threshold energy of 50-60 kev can be used to separate the two regions. Detector 14 is therefore an energy-selective detector which provides outputs 16 and 17 at the low and high energy regions respectively. Examples of such a detector will be subsequently described.

The purpose of the transmission measurement is to find the line integral of the attenuation coefficient. From the measurements of the line integral at many angles and positions, a cross-sectional image can be reconstructed of the attenuation coefficient. If a monoenergetic x-ray source is used, the detected output is given by $$I = I_0 \exp - \int \mu ds.$$

Unfortunately monoenergetic sources have inadequate strength for providing scans in reasonable time intervals. The high intensity sources, using x-ray tubes, produce polychromatic beams. These produce a detected output given by $$I = \int S(\epsilon) \exp[-\int \mu(\epsilon) ds] d\epsilon$$

where $S(\epsilon)$ is the source energy spectrum and $\mu(\epsilon)$ is the energy-dependent attenuation coefficient. Taking logs no longer provides the desired line integral of $\mu$, or its average over the spectrum, so that a distorted reconstruction results. These distortions, or spectral-shift artifacts, have seriously diminished the diagnostic value of these cross-sectional images.

The distortion would be minimized if each projection had a similar energy spectrum so that a reasonable average energy could be assigned. To accomplish this many instruments, such as the EMI head scanner, use a pathlength compensator which provides a water vessel on both sides of the object to produce a constant path length. These compensators, however, seriously increase the radiation dose to the patient since increased intensity must be applied to the patient to maintain a given detector level. Even with these compensators, however, different materials within the object, primarily bone, result in continued spectral shifts. These are minimized, in many instruments, by using relatively high energies where the bone attenuation is primarily due Compton scattering as is that of the soft tissue. This, however, removes much of the photoelectric absorption component of the attenuation coefficient which is very sensitive to atomic number. Thus the use of relatively high energies diminishes the diagnostic value of the resultant images.

In order to eliminate the spectral-shift without pathlength compensators or relatively high energies, use is made of the important face that, in the diagnostic energy range from approximately 25–150 kev, the attenuation coefficient can, with high accuracy, be decomposed into a photoelectric component which is primarily atomic-number-dependent and a Compton scattering component which is primarily density dependent. In addition, for almost all body materials, the attenuation coefficient of a cross section $\mu(x,y,\epsilon)$ can be decomposed into two basis functions given by $$\mu(x,y,\epsilon) = \frac{a_1(x,y)}{\epsilon^3} + a_2(x,y) f_{KN}(\epsilon),$$

where the first term closely represents the photoelectric component and the second term is known as the Klein-Nishina function which is an accurate representation of the Compton scattering component. It is given by $$f_{KN}(\alpha) = \frac{1+\alpha}{\alpha^2} \left[ \frac{2(1+\alpha)}{1+2\alpha} - \frac{1}{\alpha} \ln(1+2\alpha) \right] + \frac{1}{2\alpha} \ln(1+2\alpha) - \frac{(1+3\alpha)}{(1+2\alpha)^2}$$

where $\alpha$ is given by $\epsilon/510.975$ kev. The accuracy with which these two functions can be used to represent a variety of body materials is illustrated in the paper by the co-inventors which was previously referenced.

Thus each incremental region within the object 10 can be represented by an $a_1$ and an $a_2$ component. The $a_1$ or photoelectric component is approximately proportional to the fourth power of the atomic number. Thus an image of the $a_1$ values would essentially be a sensitive, atomic-number-dependent image. The $a_2$ or Compton scattering component is proportional to electron density. The electron density is essentially the same as mass density for all elements except hydrogen where it exhibits a twofold increase. Thus an image of the $a_2$ values would essentially represent a density-dependent image.

In order to compute these desirable cross-sectional images, $a_1(x,y)$ and $a_2(x,y)$, the line integrals of these components are required at many angles and positions. These are given as $$L_1 = \int a_1(x,y)ds \text{ and } L_2 = \int a_2(x,y)ds$$

$L_1$ and $L_2$ cannot be measured directly but can be computed from a low energy and high energy intensity measurement $I_1$ and $I_2$ which are the outputs 16 and 17 from energy-selective detector 14. The relationship takes the form $$I_1(L_1,L_2) = \int S(\epsilon)D_1(\epsilon)\exp\left[-\frac{L_1}{\epsilon^3} - L_2 f_{KN}(\epsilon)\right]d\epsilon$$

$$I_2(L_1,L_2) = \int S(\epsilon)D_2(\epsilon)\exp\left[-\frac{L_1}{\epsilon^3} - L_2 f_{KN}(\epsilon)\right]d\epsilon$$

where $S(\epsilon)$ is the source spectrum and $D_1(\epsilon)$ and $D_2(\epsilon)$ are the detector spectra at the low and high energy regions. We thus have two non-linear integral equations two unknowns, $L_1$ and $L_2$. Projection computer 18 solves these simultaneous equations and produces the desired line integrals where 19 is $L_1$, the atomic-number-dependent signal and 20 is $L_2$, the density-dependent signal.

The reconstruction of the cross-sectional image from its projections is now well-known in the literature. Some of the methods include the Fourier transform method, the convolution method, and the Algebraic Reconstruction Technique (ART). A general discussion of these techniques is given in the paper, "Three Methods for Reconstructing Objects From X-Rays: A Comparative Study," by G. T. Herman and S. W. Rowland in *Computer Graphics and Image Processing*, vol. 2, 1973, pages 151–178. Reconstruction computer 21 is programmed to one of these methods and used to produce the atomic-number-dependent image signal 22 and density-dependent image signal 23.

These are applied to display 24 where the two images are displayed simultaneously or in sequence. The display can represent a weighted sum of the two signals so as to emphasize the desirable aspects of each. In this case the resultant display would be comparable to that obtained with a monoenergetic source. The particular energy, however, would be under control by selection of the relative weights. Alternatively the display 24 can be a color display where each component represents a different color and is thus readily distinguishable. Thus a region of increased attenuation coefficient can be unambiguously delineated into an increased average atomic number or an increased density.

Since $L_1$ and $L_2$ are the line integrals of energy-independent components $a_1$ and $a_2$, they are completely free of spectral-shift artifacts. Therefore the resultant images not only define the materials within the cross section but are free of distorting artifacts.

FIGS. 1-*a*, 1-*b*, and 1-*c* illustrate specific embodiments of energy-selective detectors 14. In FIG. 1-*a* the transmitted x-ray beam 15 excites detector 30 which produces pulses 31 whose amplitude is proportional to energy. Detector 30 can be a crystal scintillator followed by a photo-detector or a gaseous chamber operated in the proportional mode. A single threshold is set in pulse-height analyzer 32; with pulses above that threshold amplitude being counted and forming high-energy projection signal 17, and pulses below that threshold amplitude counted and forming low-energy signal 16.

FIG. 1-*b* illustrates an integrating version of an energy-selective detector 14. Integrating detectors are often the only choice when using high counting rates where the individual pulses cannot be resolved. These high counting rates are characteristic of computerized tomography systems which use rapid scanning and achieve high density accuracy. In this system crystal scintillators 40 and 41 consist of typical scintillating material such as sodium iodide and are separated by an optically opaque layer 42 such as paper or opaque plastic. Most of the higher energy components of transmitted beam 15 will give up their energy and scintillate in crystal 41 because of their longer mean free paths. Lower energy photons, however, will give up their energy mostly in crystal 40 because of their shorter mean free path due to the greater attenuation per unit length at lower energies. None of the light from crystal 41 reaches crystal 40, and vice versa, because of light shield 42. This layer, however is relatively transparent to x-rays. Light-sensitive detector 44, such as a photomultiplier, receives the light from scintillating crystal 41 and generates high-energy projection signal 17. Light sensitive detector 43 receives the light from crystal 40 and generates low-energy projection signal 16. Unlike the system of FIG. 1-*a*, the high and low energy spectrum represented by signals 17 and 16 will have considerable overlap. Thus the $D_1(\epsilon)$ and $D_2(\epsilon)$ detector spectra have some common regions. This is taken into account, however, in projection computer 18 in FIG. 1 and does not significantly deteriorate the results.

FIG. 1-*c* illustrates an alternate form of integrating energy-selective detector 14. A gaseous ionization chamber is used which is filled with gas 35 such as Xenon or Argon. A wire with first half 37 and second half 39 is used with insulated connections to outputs 16 and 17 brought out the front and the back through sealed walls. An electric field is created between the two wire segments 37 and 39 and the chamber wall 36. Transmitted x-ray beam 15 creates ionization events within the gas 35. The electrons and ions are drawn by the field to the wire and wall, depending on the polarity. With insulator 38 separating the two wire segments 37 and 39, the outputs 16 and 17 will selectively depend on where the ionization occurs. Relatively lower energy x-ray photons will give up most of their energy in the initial portion of the chamber and thus produce low-energy projection signal 6. These lower-energy photons have a higher probability of interacting in a shorter distance since the attenuation coefficient of gas 35 is higher at the lower energies. Higher-energy photons will give up most of their energy in the further portion of the chamber and produce high-energy projection signal 17. Thus, as in FIG. 1-b, the collected x-ray photons become distributed between the lower and higher energies in a simple structure.

FIG. 1-d illustrates an embodiment of the projection computer 18. As previously indicated this computer takes the two intensity measurements representing the low and high energy projection signals, 16 and 17, and solves the previously given non-linear integral equations for the line integrals $L_1$ and $L_2$ representing the atomic-number-dependent signal 19 and the density-dependent signal 20. These integral equations can be solved by approximating them as $$\ln I_1 = b_0 + b_1 L_1 + b_2 L_2 + b_3 L_1^2 + b_4 L_2^2 + b_5 L_1 L_2 + b_6 L_1^3 + b_7 L_2^3$$

$$\ln I_2 = c_0 + c_1 L_1 + c_2 L_2 + c_3 L_1^2 + c_4 L_2^2 + c_5 L_1 L_2 + c_6 L_1^3 + c_7 L_2^3.$$

The constants $b_0, \ldots, b_7$ and $c_0, \ldots, c_7$ can be determined analytically by using known spectral responses of the x-ray sources and detectors, and the known spectral dependence of the attenuation coefficients of materials. A simple alternative is to make a number of different thicknesses. Thus eight different thicknesses of two materials are used, each having known values of $L_1$ and $L_2$. Eight pairs of intensity transmission measurements are made of $I_1$ and $I_2$, the low and high energy projection signals. The sixteen equations are used to solve for the sixteen $b$ and $c$ constants. This is done only in the initial implementation of Two-Component Polynomial Computer 54. These constants are permanently wired in and used to solve the two polynomial equations using analog or digital techniques. Although additional terms could be used for greater accuracy, the formulation shown provides sufficient accuracy for most considerations in diagnostic radiology.

The polynomial computer 54 is used on the logs of the low and high energy projection signals 16 and 17 to produce the atomic-number-dependent signal 19 and the density-dependent-signal 20. The logs are taken because of the basic exponential relationship between the desired line integrals $L_1$ and $L_2$ corresponding to 19 and 20, and the measured intensities $I_1$ and $I_2$ corresponding to 16 and 17. Thus logarithmic structures 50 and 51 are used to form signal 52, the log of low-energy projection signal 16, and signal 53, the log of high-energy projection signal 17. These structures can be digital computer systems, or analog devices such as semiconductor diodes which have a logarithmic relationship between their current and voltage.

Since the attenuation coefficient is higher at lower energies, some problem may be experienced with increased noise in the atomic-number-dependent signal 19 due to the high attenuation of the body. If it is desired to reduce the noise, it can be accomplished by sacrificing spatial resolution in that component only. If a scanned system is used, low-pass filter 55 is used to average over a few projection elements and produce a reduced-bandwidth, lower-noise signal. If a parallel array is used as with 13 in FIG. 1, this filtering is accomplished by averaging signal 19 over a number of adjacent elements.

The previous embodiments used energy-selective detectors having spectral sensitivities $D_1(\epsilon)$ and $D_2(\epsilon)$. If simpler detectors are desired, the energy selective data can be acquired in sequence. Referring to the previous simultaneous integral equations, $S(\epsilon)D_1(\epsilon)$ and $S(\epsilon)D_2(\epsilon)$ are replaced by $S_1(\epsilon)D(\epsilon)$ and $S_2(\epsilon)D(\epsilon)$ where $D(\epsilon)$ is the fixed detector spectral response and $S_1(\epsilon)$ and $S_2(\epsilon)$ are the sequence of source spectra used. FIG. 2 shows a fan-beam configuration an exemplary embodiment of sequential data acquisition. The output of x-ray source 60 is collimated into a fan or sheet beam 62 using collimator 61 which is an opaque structure with a slit. Filter wheel 63 is used to conveniently move low-energy filter 64 and high-energy filter 65 in the path of beam 62. Filter 64 can be gadolinium which has a K absorption edge at about 50 kev which forms an approximate cutoff to a low-energy filter. Filter 65 can be molybdenum which, using an appropriate thickness, provides a rounded filter response from about 50 to 100 kev. These filtered x-rays are transmitted through object 10 and measured by detector array 66. The output of detector element 67, as with all of the elements, is coupled to switch 68 which switches the detector output to a storage structure, such as a digital memory or a capacitor. Thus, when low-energy filter 64 intercepts the x-ray beam 62, switch 68 connects the detector output to storage structure 69 whose output represents low-energy projection signal 16. Similarly high-energy filter 65 is used with switch 58 connected to storage structure 70 whose output is high energy projection signal 17. Thus simultaneous projection signals are available for computer 18.

Another mechanism for changing the x-ray spectrum is that of changing the voltage on the x-ray tube. If x-ray source 60 is a conventional x-ray tube, its high-voltage supply is 59 which is controlled by control system 58. The control system can be the standard variable transformer used in high-voltage supplies. Voltage control can be used as the sole means of varying the energy spectrum, with filter wheel 63 not used, and lower voltages used for low-energy projection signal 16 and higher voltages for high-energy projection signal 17, with switch 68 switched accordingly. For improved results, however, high voltage control 58 can be used in combination with filter wheel 63 to provide a higher degree of spectral delineation between the lower and higher energy spectra.

Figure 3:
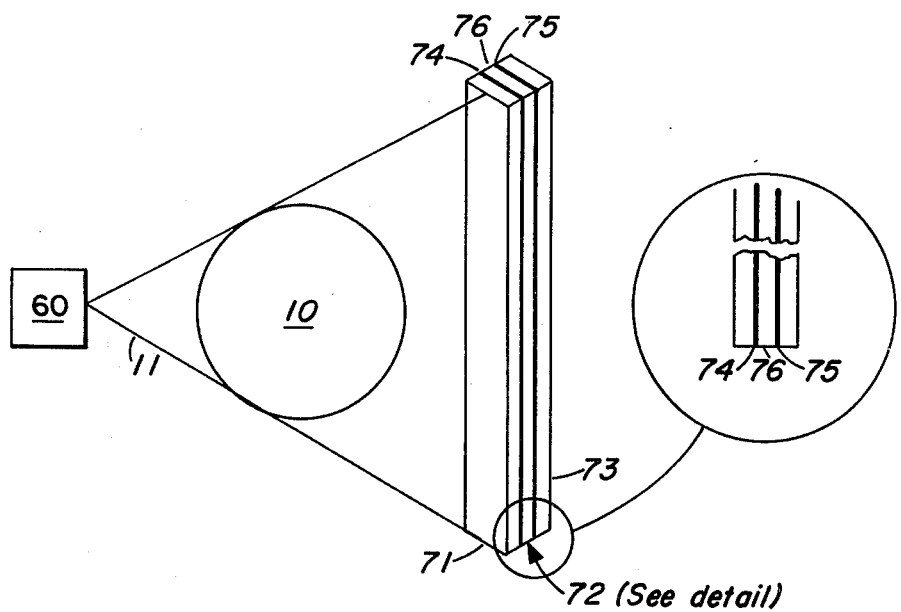
FIG. 3 is a schematic representation of an embodiment using a two-dimensional detector.
Figure 4:
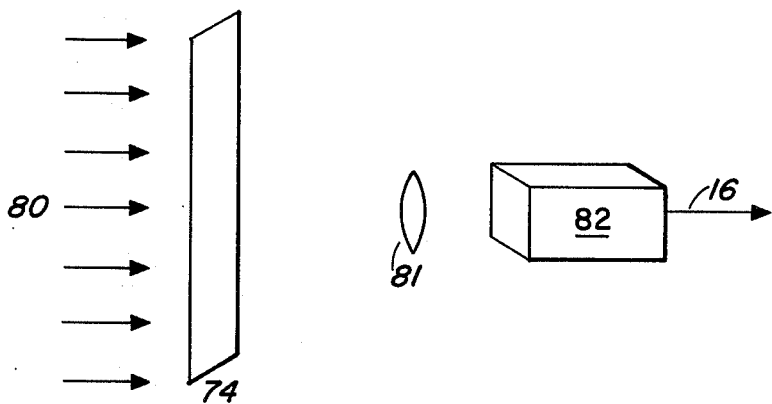
FIG. 4 is a schematic representation of a scanner for reading the projection information.

The systems illustrated thusfar have investigated a single section through object 10. In FIG. 3, a two-dimensional projection is obtained through the volume of object 10, thus simultaneously measuring projections at many cross sections. If this data is taken at many angles, the entire three-dimensional volume can be reconstructed. To achieve the important advantages of spectral decomposition a two-dimensional energy selective detector can be used. As shown in FIG. 3, two scintillating phosphor layers 71 and 73 are used with double-emulsion film 72 sandwiched between them. These scintillating phosphors can, for example, be similar to the calcium tungstate screens used in conventional radiography. The relatively low-energy photons will interact primarily in phosphor 71 while the higher energy photons will interact primarily in phosphor 73. The double emulsion film is separated by an opaque layer 76 which is transparent to x-rays. The emulsion 74 records low-energy transmission information and emulsion 75 records high-energy transmission information. These are developed, separated, and scanned to provide the desired projection signals. As shown in FIG. 4 developed transparency 74 is illuminated by light source 80 and imaged onto television camera 82 using lens 81. When the transparency 74 is scanned it produces low-energy transmission signal 16 over an entire plane. Similarly developed transparency 75 will generate high-energy transmission signal 17. These signals are stored and used in the system of FIG. 1 to reconstruct each cross section in the entire volume.

The two-dimensional data can be acquired in sequence by using filter wheel 63 and/or high voltage control 58 of FIG. 2 to sequentially change the spectrum in the system of FIG. 3. In that case a simple detector can be used such as scintillating phosphor 71 and emulsion 74. Two emulsions are exposed in sequence using the sequential energy spectra and a mechanism for changing the film. The resultant developed emulsions are again scanned in sequence as is shown in FIG. 4.

To provide simultaneous outputs for the low and high energy transmission signals, double-emulsion film 72 can be color film with at least two separate color-sensitive emulsions 74 and 75. Scintillating phosphor screens 71 and 73 can be designed to provide different colors or color filters can be placed between these screens and the emulsions. Thus a two-color transparency is produced with each color representing the transmission at a given spectrum. This can be illuminated as in FIG. 4 with camera 82 being a color-sensitive camera producing at least two output signals representing each color. The output signals corresponding to the scanned two-color transparency simultaneously represent the low and high energy transmission signals, 16 and 17.

The systems of FIGS. 3 and 4 have been described in terms of providing energy selective two-dimensional projection which are subsequently used, with other projections at many angles, to provide three-dimensional reconstructions. However, the processed projection information itself can be a valuable addition to conventional single-projection radiography. Projections can be obtained by one of the variations of FIGS. 3 and 4 to obtain low and high energy transmission signals representing the two-dimensional projection information. This information can be processed, as in the projection computer 18 of FIG. 1, to obtain atomic number-dependent and density-dependent signals 19 and 20. These can then be used in a display or printer to form separate images of this processed information. Although these will be projection images, with many planes superimposed, they do provide increased information. For example, the density-dependent image derived from 20 will be relatively free of bone and concentrate primarily on soft tissue. It will thus be useful in displaying various lesions, such as tumors, which underlie bone. Various combinations of the two images can be used to enhance or suppress specific materials. For example, with the right combination of the two processed signals, 19 and 20, materials such as bone can be made to completely disappear.

In the spectral decomposition we have used, the photoelectric component, which is atomic-number dependent, was closely approximated by $a_1/\epsilon^3$ in the region of interest. For greater accuracy, it may be beneficial to use more complex representations such as $a_0/\epsilon^3 + a_1/\epsilon^4$. In that case, an additional transmission measurement must be made to evaluate the new component. Thus a total of three projection signals would be required, two in the lower energy regions, and one in the high energy region, to provide the three component decomposition.

The systems discussed thusfar have been capable of performing two improvements in cross-sectional imaging systems, the removal of spectral-shift artifacts and the production of two reconstructed images which define the specific material characteristics of each element in the cross section. In some systems only a single undistorted image is required. In that case, referring to FIG. 1, the low-energy and high-energy projection signals, 16 and 17, are used in projection computer 18 to form a single processed signal 19, with signal 20 not utilized. This processed signal 19 will, in general, be the line integral of an energy-independent component. Thus signal 19 could be either $L_1$, the line integral of $a_1$, the atomic-number-dependent component, or $L_2$, the line integral of $a_2$, the density-dependent component. Alternatively processed signal 19 could represent some other combination of these two which would also be energy-independent. In that case the attenuation coefficient $\mu(E)$ would have effectively been decomposed into a different set of two functions. The single processed signal 19, obtained at a plurality of angles, is then used in reconstruction computer 21 to produce reconstruction image signal 22. As previously mentioned, signal 22 can represent either an atomic-number-dependent image signal, a density-dependent image signal, or some combination of the two. Display 24 becomes a single component display producing an image free of spectral-shift artifacts.

What is claimed is:

1. Apparatus for providing energy-dependent x-ray images of an object comprising:
   an x-ray source positioned on one side of the object producing an x-ray beam which transverses the object;
   an x-ray detector positioned on the side of the object opposite that of the source;
   means for measuring the x-ray transmission through the object, with the x-ray detector, at the lower and higher energy regions of the diagnostic x-ray spectrum and producing a low-energy projection signal and a high-energy projection signal;
   computational means for processing the low-energy projection signal and the high-energy projection signal and producing an atomic-number-dependent signal which is substantially on the line integral of the atomic number of the object raised to a power, and a density-dependent signal which is substantially dependent on the line integral of the density of the object; and
   means for utilizing a plurality of the atomic-number-dependent signal and a plurality of the density-dependent signal to produce energy-dependent x-ray images of the object.

2. Apparatus as recited in claim 1 including means for making x-ray transmission measurement through the object at a plurality of angles and producing at each of the angles a plurality of atomic-number-dependent signals and density-dependent signals and wherein the means for utilizing the atomic-number-dependent signals and the density-dependent signals comprises:
   means for reconstructing cross-sectional atomic-number-dependent and density-dependent images of the object using the plurality of atomic-nubmer-dependent and density-dependent signals representing different angles; and
   means for displaying the atomic-number-dependent and density-dependent cross-sectional images.

3. Apparatus as recited in claim 2 wherein the means for displaying the atomic-number-dependent and density-dependent cross-sectional images includes means for obtaining a weighted sum of the two images whereby a composite image is produced representing a specific energy.

4. Apparatus as recited in claim 2 wherein the means for displaying the atomic-number-dependent and density-dependent cross-sectional images includes a composite color display where each image is represented by a different color.

5. Apparatus as recited in claim 1 wherein the means for measuring the x-ray transmission through the object at the lower and higher energies of the diagnostic x-ray spectrum includes means for sequentially changing the energy spectrum of the x-ray source to the lower and higher energies and storing the resultant output of the x-ray detector to sequentially produce the low and high energy projection signals.

6. Apparatus as recited in claim 5 wherein the means for sequentially changing the energy spectrum of the x-ray source includes means for sequentially placing a first and second filter between the x-ray source and the object to pass primarily the desired low and high energy regions of the energy spectrum and attenuate the undesired regions.

7. Apparatus as recited in claim 5 wherein the x-ray source includes an x-ray tube powered by a high-voltage supply and the means for sequentially changing the energy spectrum of the x-ray source includes means for sequentially changing the output of the high-voltage supply.

8. Apparatus as recited in claim 1 wherein the x-ray source emits an energy spectrum within the diagnostic energy range and the x-ray detector is energy selective.

9. Apparatus as recited in claim 8 wherein the x-ray detector includes a pulse-height analyzer with pulses exceeding a threshold forming the high-energy projection signal and pulses not exceeding the threshold forming the low-energy projection signal.

10. Apparatus as recited in claim 8 wherein the x-ray detector is divided into a first section representing the initial material traversed by the x-ray beam and a second section representing the remaining material traversed by the x-ray beam and including means for separately detecting the outputs of the first and second sections to produce the low energy and high energy projection signals.

11. Apparatus as recited in claim 10 wherein the material is a scintillator and the means for separately detecting the outputs of the first and second sections are light-sensitive detectors separately optically coupled to the first and second sections.

12. Apparatus as recited in claim 10 wherein the material is a gas and the means for separately detecting the outputs of the first and second sections are electrically isolated connections for collecting the charge produced in each section.

13. Apparatus as recited in claim 1 wherein the x-ray detector is a two-dimensional image-producing structure for recording a two-dimensional projection through the object.

14. Apparatus as recited in claim 13 wherein the means for measuring the x-ray transmission through the object at the lower and higher regions of the diagnostic x-ray energy spectrum includes means for sequentially changing the energy spectrum of the x-ray beam between the two energy regions and recording the resultant images, and the means for producing low-energy and high-energy projection signals includes a scanner for scanning the recorded images.

15. Apparatus as recited in claim 13 wherein the x-ray detector includes two parallel scintillating layers and the means for measuring the x-ray transmission through the object at the lower and higher energy regions includes a pair of light-sensitive recorders which are coupled to each of the two scintillating layers and the means for producing low-energy and high-energy projection signals includes a scanner for scanning each of the recorded images.

16. Apparatus as recited in claim 1 wherein the computational means includes means for solving two simultaneous integral equations where each equation is the projection signal set equal to the integral, over the energy spectrum of the x-ray beam and the x-ray detector, of the exponent of minus the atomic-number-dependent signal multiplied by its energy dependence minus the density-dependent signal multiplied by its energy dependence.

17. Apparatus as recited in claim 16 wherein the means for solving the two simultaneous integral equations includes means for solving two simutaneous polynomial equations where each polynomial equation is the log of the projection signal set equal to the sum of a plurality of terms where each term is the product of a constant term, the atomic-number-dependent signal raised to an integer power, and the density dependent signal raised to an integer power.

18. Apparatus as recited in claim 1 wherein the computational means includes means for filtering the atomic-number-dependent signal whereby the noise components in this signal are reduced.

19. Apparatus for producing a cross-sectional x-ray image of an object comprising:
a polychromatic x-ray source positioned on one side of the object producing an x-ray beam;
an x-ray detector positioned on the side of the object opposite that of the source;
means for measuring the x-ray transmission through the object with the x-ray detector at lower and higher energy regions of the diagnostic x-ray spectrum at a plurality of angles and producing a plurality of low-energy projection signals and a plurality of high-energy projection signals;
computational means for processing each of the low-energy projection signals and high-energy projection signals to produce a plurality of processed signals which are the line integrals of an energy-dependent component; and
means for utilizing the processed signals to reconstruct the cross-sectional image of the object which is free of spectral artifacts.

20. Apparatus as recited in claim 19 wherein the computational means produces processed signals which are density-dependent signals representing the Compton scattering component of the attenuation coefficient.

21. Apparatus as recited in claim 19 wherein the computational means produces processed signals which are atomic-number-dependent signals representing the photoelectric absorption component of the attenuation coefficient.

22. Apparatus as recited in claim 19 wherein the computational means produces processed signals which represent a combination of the Compton scattering and photoelectric absorption components of the attenuation coefficient.

* * * * *